(12) United States Patent
Smudde

(10) Patent No.: US 10,258,761 B2
(45) Date of Patent: Apr. 16, 2019

(54) CHILDREN'S PRODUCT WITH SYNCHRONIZED SOUND AND NON-SOUND OUTPUT

(71) Applicant: GRACO CHILDREN'S PRODUCTS INC., Atlanta, GA (US)

(72) Inventor: Bart A. Smudde, Cumming, GA (US)

(73) Assignee: GRACO CHILDREN'S PRODUCTS INC., Atlanta, GA (US)

( * ) Notice: Subject to any disclaimer, the term of this patent is extended or adjusted under 35 U.S.C. 154(b) by 366 days.

(21) Appl. No.: 15/098,020

(22) Filed: Apr. 13, 2016

(65) Prior Publication Data
US 2016/0303344 A1    Oct. 20, 2016

Related U.S. Application Data

(60) Provisional application No. 62/148,727, filed on Apr. 16, 2015.

(51) Int. Cl.
| | |
|---|---|
| *A61M 21/02* | (2006.01) |
| *A47D 13/10* | (2006.01) |
| *A47D 9/02* | (2006.01) |
| *H04R 1/02* | (2006.01) |
| *A61M 21/00* | (2006.01) |

(52) U.S. Cl.
CPC ............. *A61M 21/02* (2013.01); *A47D 9/02* (2013.01); *A47D 13/10* (2013.01); *A61M 2021/0022* (2013.01); *A61M 2021/0027* (2013.01); *A61M 2021/0044* (2013.01); *A61M 2021/0061* (2013.01); *A61M 2205/3561* (2013.01); *A61M 2205/3584* (2013.01);
(Continued)

(58) Field of Classification Search
CPC ....... A61M 21/00–21/02; A47D 13/10–13/107
See application file for complete search history.

(56) References Cited

U.S. PATENT DOCUMENTS

| | | | |
|---|---|---|---|
| 7,039,207 B1 * | 5/2006 | Elrod | A47C 7/72 381/301 |
| 7,905,791 B2 | 3/2011 | Guang et al. | |

(Continued)

FOREIGN PATENT DOCUMENTS

| | | |
|---|---|---|
| CN | 102846094 A | 1/2013 |
| CN | 102894731 A | 1/2013 |
| CN | 103368481 A | 10/2013 |

*Primary Examiner* — Thaddeus B Cox
(74) *Attorney, Agent, or Firm* — Eversheds Sutherland (US) LLP

(57) ABSTRACT

A children's soothing device, such as a motorized swing, a motorized glider, a motorized rocker, a motorized bouncer, a playard, a crib, a car seat, a stroller, an infant carrier, or a bassinet, can include one or more speakers, one or more vibrating motors or solenoids, and one or more light attractions or lights for soothing a child. The children's soothing device can include a control system for storing and reading sound and other data files to output music or other sounds through the speakers and to activate and deactivate the vibrating motors in a synchronized pattern with the sound or music. The children's soother device can also evaluate the sound and other data files to synchronize the activation, deactivation, and/or change of state of the light attraction or lights with the sound/music and the vibrating motors.

20 Claims, 18 Drawing Sheets

(52) U.S. Cl.
CPC .............. *A61M 2205/3592* (2013.01); *A61M 2205/502* (2013.01); *H04R 1/028* (2013.01); *H04R 2400/03* (2013.01)

(56) References Cited

U.S. PATENT DOCUMENTS

| | | |
|---|---|---|
| 8,308,578 B2 | 11/2012 | Gilbert et al. |
| 8,602,903 B2 | 12/2013 | Gilbert |
| 8,661,582 B2 | 3/2014 | Sclare et al. |
| 8,708,832 B2 | 4/2014 | Gilbert et al. |
| 8,757,716 B2 | 6/2014 | Ru et al. |
| 8,783,769 B2 | 7/2014 | Gilbert et al. |
| 8,784,225 B2 | 7/2014 | Burns et al. |
| 8,834,282 B2 | 9/2014 | Sclare et al. |
| 2011/0105237 A1* | 5/2011 | Gillett .................. A47D 13/105 472/118 |
| 2013/0134752 A1 | 5/2013 | Gilbert et al. |
| 2014/0068859 A1 | 3/2014 | Alegria |
| 2014/0123386 A1 | 5/2014 | Scalre et al. |
| 2014/0221112 A1 | 8/2014 | Gilbert et al. |
| 2014/0265480 A1* | 9/2014 | Perrin ...................... B60N 2/26 297/217.4 |
| 2014/0306498 A1 | 10/2014 | Gilbert et al. |

* cited by examiner

CHILDREN'S PRODUCT WITH SYNCHRONIZED SOUND AND NON-SOUND OUTPUT

CROSS-REFERENCE TO RELATED APPLICATION

This application claims priority under 35 U.S.C. § 119 to U.S. Provisional Patent Application No. 62/148,727 filed Apr. 16, 2015, and titled "Synchronization of Sound Output and Non-Sound Output in a Soothing System for Children's Products," the entire contents of which are hereby incorporated herein by reference for all purposes.

BACKGROUND

Baby swings, bouncers, rockers, playards, and other such children's products may sometimes be provided with a device, mechanism, or system that produces soothing music, nature sounds, white noise, and/or vibration. These types of products may be configured to help soothe a child using the product. Sounds such as music or nature sounds may be played or delivered while a child occupies the product in order to help soothe the child. In addition, all or portions of the product may be vibrated to help soothe the child. Further, one or a series of lights may be activated and deactivated to help soothe the child. However, conventional children's products only provide an always on or always off option to the parent or guardian to play the sounds and lights, and/or to activate the vibration mechanism. For example, if the vibration mechanism is activated, the product will vibrate constantly until the parent or guardian deactivates the vibration mechanism. Similarly, if the lights are turned on by the parent or guardian, the lights will activate and deactivate according to a predetermined pattern for as long as the lights are left on by the parent or guardian. While vibration and lights at the product may soothe the child, constant vibration and light operation may not be desired as it may overstimulate the child or irritate the child. Further, having the ability to synchronize the vibration and lights to the music, such that they only activate at predetermined times during the playing of the music may provide an improved soothing aspect for the child using the product.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. The term "or" is used herein in both the alternative and conjunctive sense, unless otherwise indicated. The terms "illustrative," "example," and "exemplary" are used to be examples with no indication of quality level. Like numbers refer to like, but not necessarily the same or identical, elements throughout.

Figure 1:
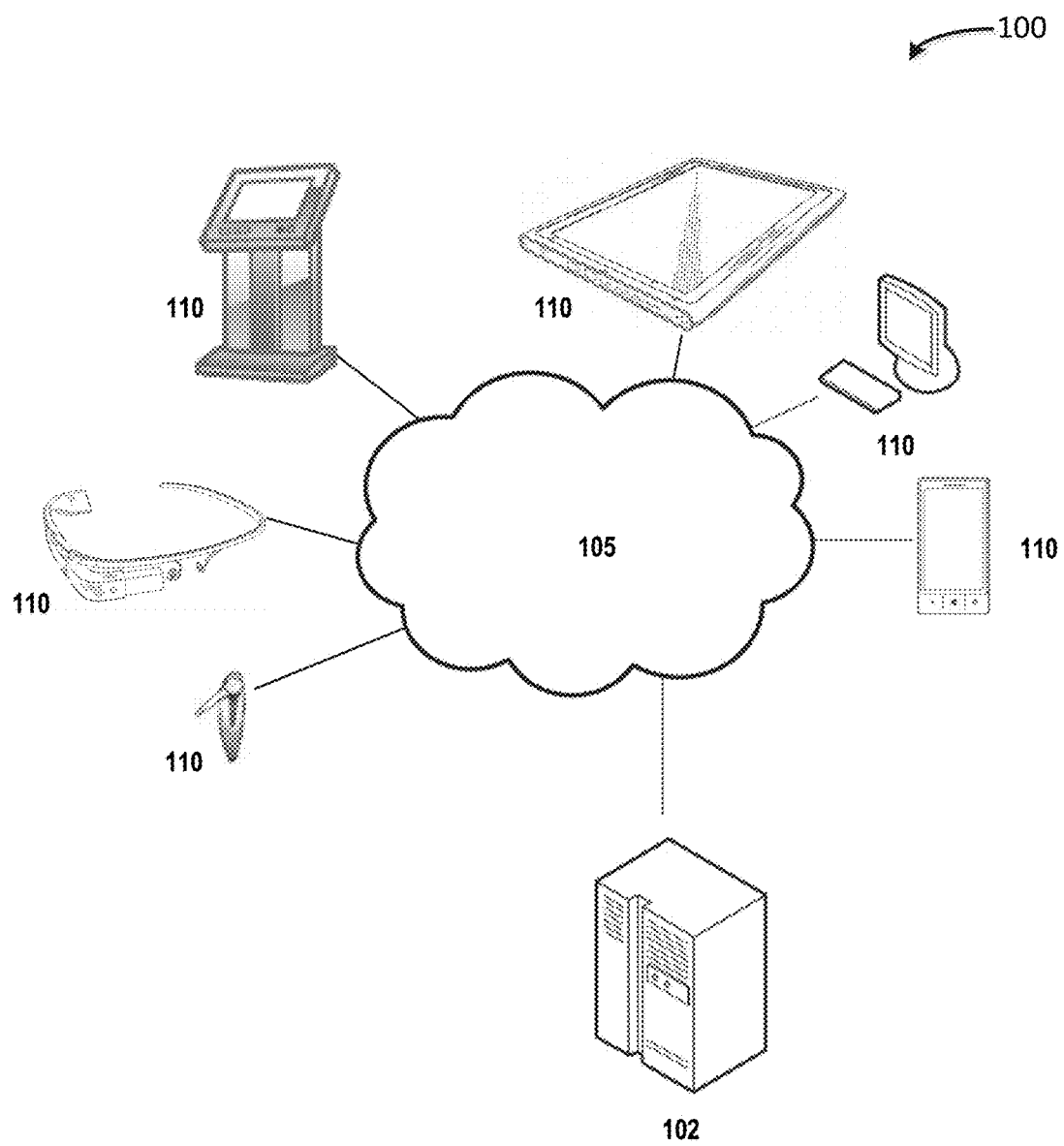
FIG. 1 is an overview of a system for synchronizing sound and non-sound output in an infant swing or other children's product according to one example embodiment of the disclosure.

As should be appreciated, the example embodiments described herein may be implemented as methods, apparatus, systems, and/or the like. FIG. 1 is an overview of an example system 100 for synchronizing sound and non-sound output (e.g., lights and/or vibration) in an infant swing or other children's soothing device (e.g., motorized swing, motorized glider, motorized rocker, motorized bouncer, playard, crib, car seat, stroller, infant carrier, or bassinet) according to one example embodiment of the disclosure. Referring to FIG. 1, example system 100 may include one or more management computing entities 102, one or more networks 105, and one or more user computing entities 110. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

Figure 2:
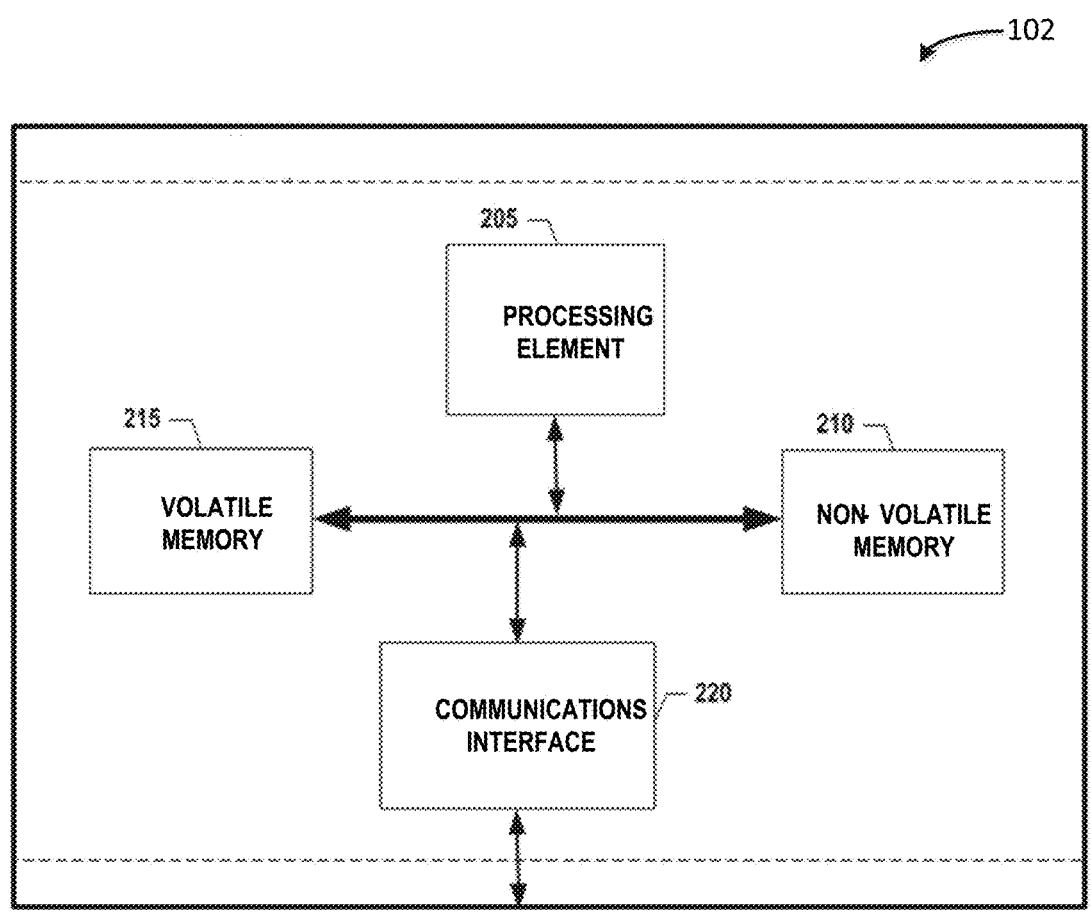
FIG. 2 is a schematic diagram of a management computing entity according to one example embodiment of the disclosure.

FIG. 2 is a schematic diagram of a computing device for synchronizing sound and non-sound output according to one example embodiment of the disclosure. Now referring to FIGS. 1 and 2, the example management computing entity 102 may be embedded in any of the one or more children's soothing device (e.g., motorized swing, motorized glider, motorized rocker, motorized bouncer, playard, crib, car seat, stroller, infant carrier, or bassinet). In other example implementations, the management computing entity 102 is a computing entity that is in communication with a children's soothing device. As indicated in FIG. 2, in one example embodiment, the management computing entity 102 may include one or more communications interfaces 220 for communicating with various other computing entities, such as by communicating data, content, information, and/or similar terms used herein interchangeably that can be transmitted, received, operated on, processed, displayed, stored, and/or the like. For instance, the management computing entity 102 may communicate with user computing entities 110.

The management computing entity 102 may include or be in communication with one or more processing elements 205 (e.g., microprocessors, processors, processing circuitry, etc.) that communicate with other elements within the management computing entity 102 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. In certain example embodiments, the processing element 205 is embedded in a children's soothing device, and may be embodied as one or more integrated circuits, application specific integrated circuits (ASICs), field programmable gate arrays (FPGAs), programmable logic arrays (PLAs), hardware accelerators, and/or the like. The processing element 205 may be configured to execute instructions stored in volatile or non-volatile memory and may be capable of performing steps or operations according to the example embodiments discussed herein.

In one example embodiment, the management computing entity 102 may also include or be in communication with non-volatile memory 210. In certain example embodiments, the non-volatile memory 210 may include one or more of hard disks, read-only memory (ROM), programmable ROM (PROM), erasable PROM (EPROM), electrically EPROM (EEPROM), flash memory, multimedia cards (MMCs), secure digital (SD) memory cards, memory sticks, and/or the like. In one embodiment, the management computing entity 102 may further include or be in communication with volatile memory 215. In one embodiment, the volatile memory 215 may include one or more of random access memory (RAM), dynamic RAM (DRAM), static RAM (SRAM), cache memory, and/or the like.

The management computing entity 102 may also include one or more communications interfaces 220 for communicating with various computing entities, such as by communicating data, content, and/or information either via wire or wirelessly, such as, for example, Wi-Fi, infrared (IR) protocols, near field communication (NFC), Bluetooth, or any other wireless protocol.

Although not shown, the management computing entity 102 may include or be in communication with one or more input elements, such as a keyboard, mouse, touch screen/display, audio input, pointing device, or the like. As will be appreciated, one or more components of the management computing entity 102 may be located remotely from other management computing entity components, such as in a distributed system. Furthermore, one or more of the components may be combined and additional components performing functions described herein may be included in the management computing entity 102. As will be recognized, these architectures and descriptions are provided for exemplary purposes only and are not limiting to the various embodiments.

Figure 3:
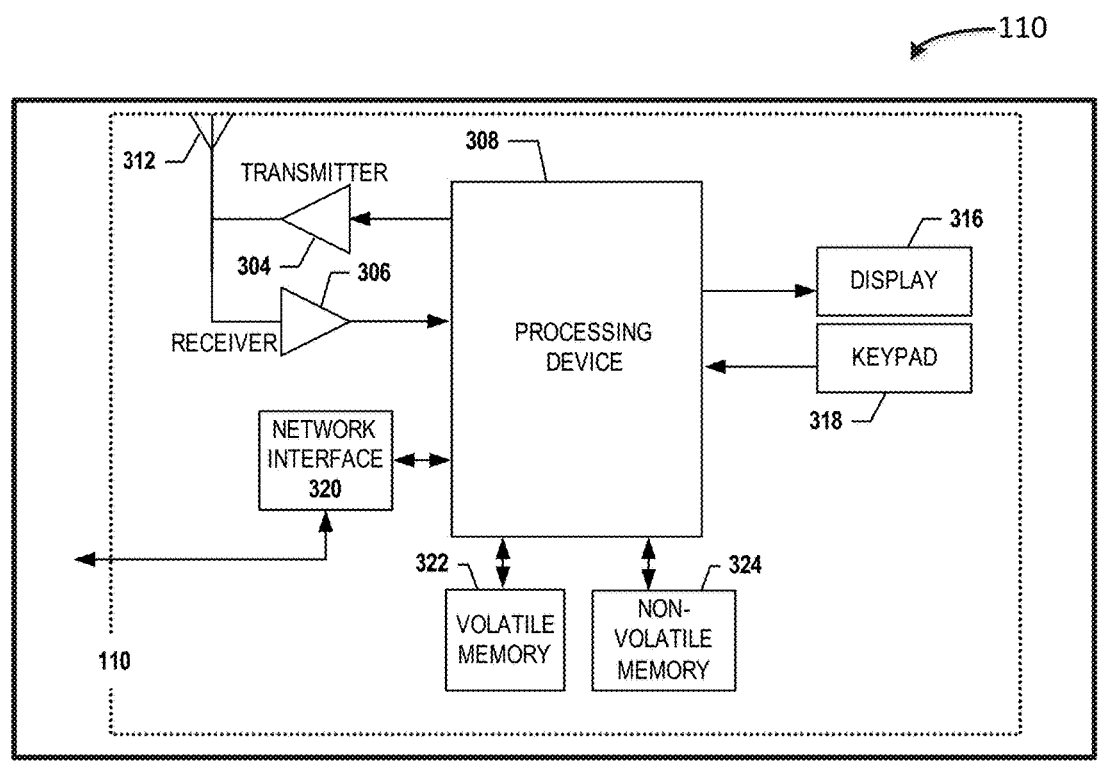
FIG. 3 is a schematic diagram of a computing device for synchronizing sound and non-sound output according to one example embodiment of the disclosure.

A user (e.g., parent or guardian) may operate a user computing device 110 that includes one or more components that are functionally similar to those of the management computing entity 102. FIG. 3 provides an illustrative schematic of a user computing device 110 for synchronizing sound and non-sound output at the children's soothing device according to one example embodiment of the disclosure. Referring to FIG. 3, the user computing device 110 can include, but is not limited to a laptop/desktop computer, smart phone, tablets, phablets, notebooks, or the like. The user computing device 110 can include an antenna 312, a transmitter 304 (e.g., radio), a receiver 306 (e.g., radio), and a processing element 308 (e.g., microprocessors, multi-core processors, coprocessing entities, ASIPs, microcontrollers, and/or controllers) that provides signals to and receives signals from the transmitter 304 and receiver 306, respectively. The user computing device 110 may operate in accordance with any of a number of wireless communication standards and protocols, such as those described above with regard to the management computing entity 102. Similarly, the user computing device 110 may operate in accordance with multiple wired communication standards and protocols via a network interface 320.

The user computing device 110 may also comprise a user interface that can include a display 316 and/or a user input interface. For example, the user interface may be a user application executing on and/or accessible via the user computing device 110 to interact with the management computing entity 102. The user input interface can include, but is not limited to, a keypad 318, a touch display, voice/speech or motion interfaces, or other input device. In certain example embodiments, the input may be used to control the soothing system remotely.

The user computing device 110 can also include volatile memory 322 and/or non-volatile memory 324. The memory of the user computing device 110 may include a user application that is resident on the device 110 or accessible through a browser or other user interface for communicating with the management computing entity 102 and/or various other computing entities.

Exemplary System Operation

Motorized swings, motorized gliders, motorized rockers, motorized bouncers, playards, cribs, car seats, strollers, infant carriers, bassinets, and other such children's soothing devices can include one or more devices, mechanisms, or systems that produces music, nature sounds, white noise, and vibration to help soothe a child using the device. The children's soothing device can also include one or more colored or clear lights or lighting arrays that are visible to the child when positioned in the device. These lights or lighting arrays can also be controllably illuminated to assist in soothing the child.

In certain example embodiments, one or more direct current (DC) motors with offset or out-of-balance weights is used to provide vibration to the children's soothing device. The vibrating motor or motors are often attached to the seat of the swing or internal to the playard frame or play surface or other vibrating device in a manner so that the child can feel the vibrations. In some examples, multiple levels or intensities of vibration that can be selected by the parent or guardian.

Music can also be played by the children's soothing device. The music may be generated by electronic devices that are built into a portion of the children's soothing device, such as a housing coupled to the frame of the soothing device.

As described above, the disclosed soothing device can be configured to deliver synchronized non-sound and sound output generated by the system. In one example, the disclosed soothing device can be configured to synchronize sounds and vibration detectable to a child occupying the children's soothing device. In one example, the sounds can include music, a heartbeat or simulated heartbeat, nature sounds, white noise, a car ride, a stroller ride (e.g., sound of the stroller wheels along the ground with or without nature sounds), rain, wind, waves or other ocean or beach-related sounds, playful sounds, bells, and/or the like. In one example, the disclosed soothing device can, in addition or in the alternative, be configured to deliver synchronized vibration and lights to a child occupying a children's soothing device. In addition or in the alternative, the children's soothing device can be configured to deliver synchronized sounds or music with vibration and lights to a child occupying a children's soothing device. Other combinations of music, sounds, light, and/or vibration may also be employed in the disclosed soothing device.

As described above, the management computing entity 102 and/or user computing device 110 may be configured to control and/or transmit information to a children's soothing device. In one example embodiment, the management computing entity 102 may synchronize operation of the vibrating motors and/or lighting system of the soothing device with music. In one example embodiment, the music is played through one or more audio devices (e.g., speakers) that are part of or attached to the children's soothing device. In other example embodiments, music (and optionally the associated synchronization of the vibrating motors and/or lighting system) may be loaded (wired or wirelessly) from the user computing device 110 onto the children's soothing device. For example, music may be loaded into the memory of children's soothing device via one or more cables for playback at a later time.

In one example embodiment, the management computing entity 102 may synchronize lights of the soothing device with music. For example, the lights on the children's soothing device may turn on and off according to the music. In another example, the lights may change color based on the music.

Figure 4:
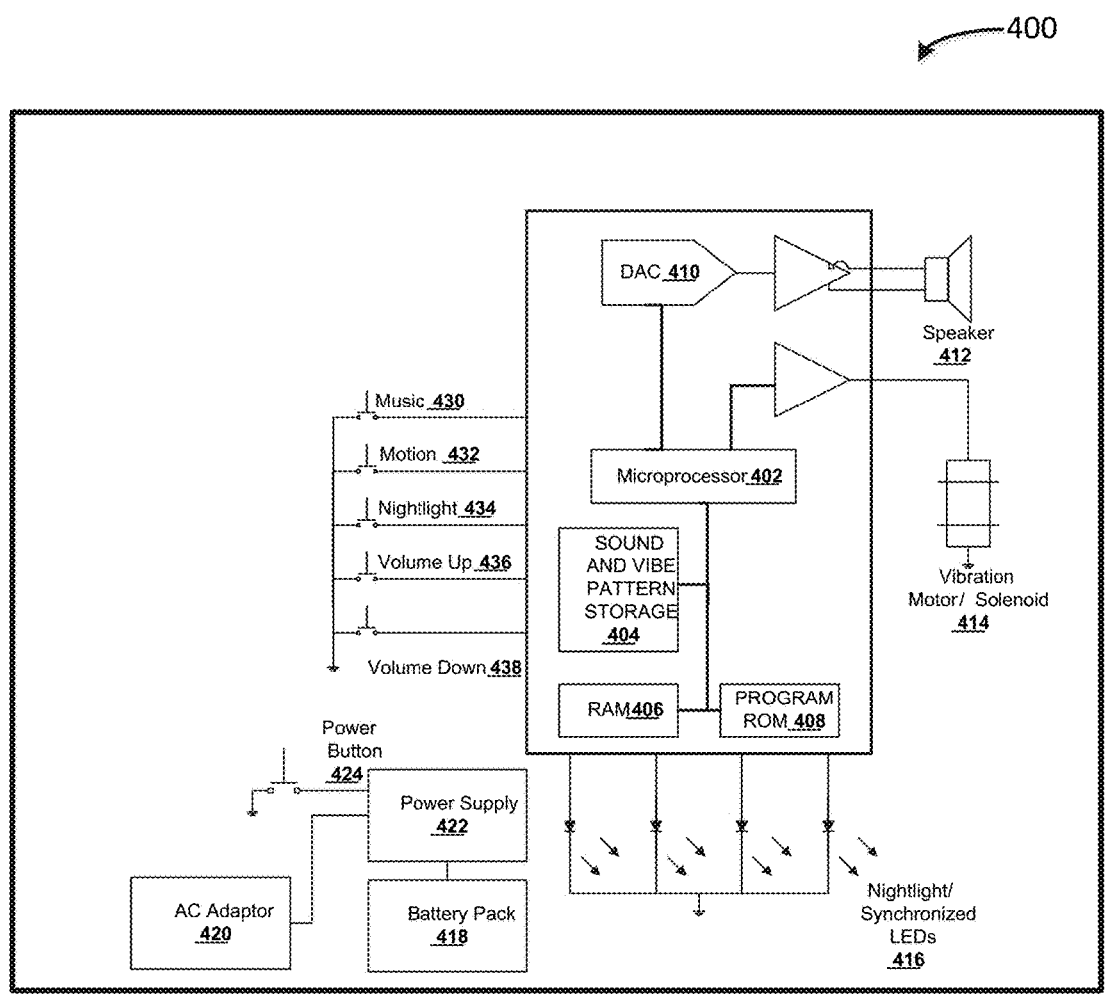
FIG. 4 is a schematic diagram of a control system at a baby swing or other children's product for synchronizing sound and non-sound output at the children's product according to one example embodiment of the disclosure.

FIG. 4 is an exemplary schematic diagram of a control system 400 for a children's soothing device (e.g., motorized swing, motorized glider, motorized rocker, motorized bouncer, playard, crib, car seat, stroller, infant carrier, or bassinet) according to one example embodiment of the disclosure. In this example embodiment, the management computing entity 102 is a microprocessor, in communication with one or more types of memory (e.g., RAM 406 and/or program ROM 408), and is embedded in or attached to the children's soothing device. Further, in this example embodiment, the memory is also embedded or attached to the children's soothing device.

Referring to FIG. 4, the example control system 400 can include a sound and vibration pattern storage medium 404. In one example, the sound and vibration pattern storage medium 404 may be a hard disk configured for storing one or more media files and information associated with the media files. For example, a media file may be a Musical Instrument Digital Interface (MIDI) file that includes one or more non-sound event markers. In certain example embodiments, the media files may include one or more MP3 files, WAV files, FLAC files, ZAB files, 3GA files, CDA files, MPEG-4 files, WMA files, and/or the like. In some examples, each media file may include one or more markers identifying a time for initiating one or more non-sound events. For example, the marker may be a time indicator for turning on or turning off the vibration motor(s) of the children's soothing device.

The exemplary children's soothing device can include a plug to connect the children's soothing device to a household's AC electrical supply. Alternatively or in addition, the system can have a power supply 422 and an AC adaptor 420 with a battery pack 418 so as to operate the children's soothing device independent of a connection to a household AC source. The battery pack 418 can include one or more batteries and can be replaceable and/or rechargeable. The children's soothing device can also include a power button 424 or switch to turn the children's soothing device on and off.

The microprocessor 402 can be communicably coupled to one or more speakers 412 disposed on or removably coupled to the children's soothing device. For example, each speaker 412 can be disposed in a control housing or along the frame of the children's soothing device or may be movable or adjustable to change positions along the children's soothing device.

The children's soothing device can include a volume control function 436, 438 by which a user can raise 436 or lower 438 the volume of the sounds and/or music emanating from the one or more speakers 412. The children's soothing device can also include multiple speakers 412. In one example, the children's soothing device may include a music control element 430 (e.g., radio button, dial, switch, etc.) for turning on/off the music or sound playback through the speakers 412. The example speakers 412 may be digital or analog, amplified or non-amplified. As shown in FIG. 4, the speakers 412 are communicably coupled to a digital to analog (DAC) converter 410 that facilitates conversion of the output signal of microprocessor 402 from a digital signal to an analog signal configured for playback at speaker 412.

The microprocessor 402 can also be communicably coupled to a vibration motor/solenoid 414 and programmed and configured to control the vibration motor/solenoid by turning the vibration motor/solenoid 414 on and off in a predetermined or desired pattern. Movement and vibrations can be generated in a number of ways by the vibration motor/solenoid 414. In one example, one or more vibration motors/solenoids 414 can be coupled to the children's soothing device in close proximity to the child contacting surface such that a child occupying the device can feel the vibrations produced by the motor 414. For example, the vibration motor/solenoid 414 can be housed under a seat, play surface, sleeping surface, or other child contacting surface on the children's soothing device. In another example, one or more vibrating DC motors 414 may be used. For example, one or more solenoid(s) 414 with weights could generate movement through one axis rather than two axes (vibrating motor 414) to produce a physical motion or vibration detectable by a child positioned on or within the children's soothing device. The example solenoid(s) 414 may be used to simulate a mother patting the child's back (such as to simulate burping or a soothing pat, etc.). The vibration motor/solenoid 414 may be connected to and powered by a power supply 422 on the children's soothing device or electrically coupled to the children's soothing device.

Additionally, the microprocessor 402 may be communicably coupled to one or more lights 416 (e.g., light emitting diodes (LEDs), nightlights, colored lights, light arrays, etc.) and programmed and configured to turn one or more of the lights 416 on and off in a desired or predetermined pattern. The lights or light source 416 can include lights of different brightness and/or different colored lights, and/or different types of lights. The lights 416 can include one or more different color LEDs, for example. The light source 416 can be synchronized with the sound output in the same manner described above for the vibrations. In one example, the lights 416 can be positioned and arranged on the children's soothing device or on a removable attachment to the device so that a child occupying the product can see the lights 416 directly, or sees indirect light produced by the lights 416, while on the child contacting surface of the children's soothing device.

In certain example embodiments, the children's soothing device may also include a motion activation control element 432. The motion control element 432 may be configured to activate and deactivate motion (e.g., swinging motion, rocking motion, circular motion, another patterned or random motion, vibration (high vibration, low vibration, etc.)) of all or a portion of the children's soothing device.

Figure 5:
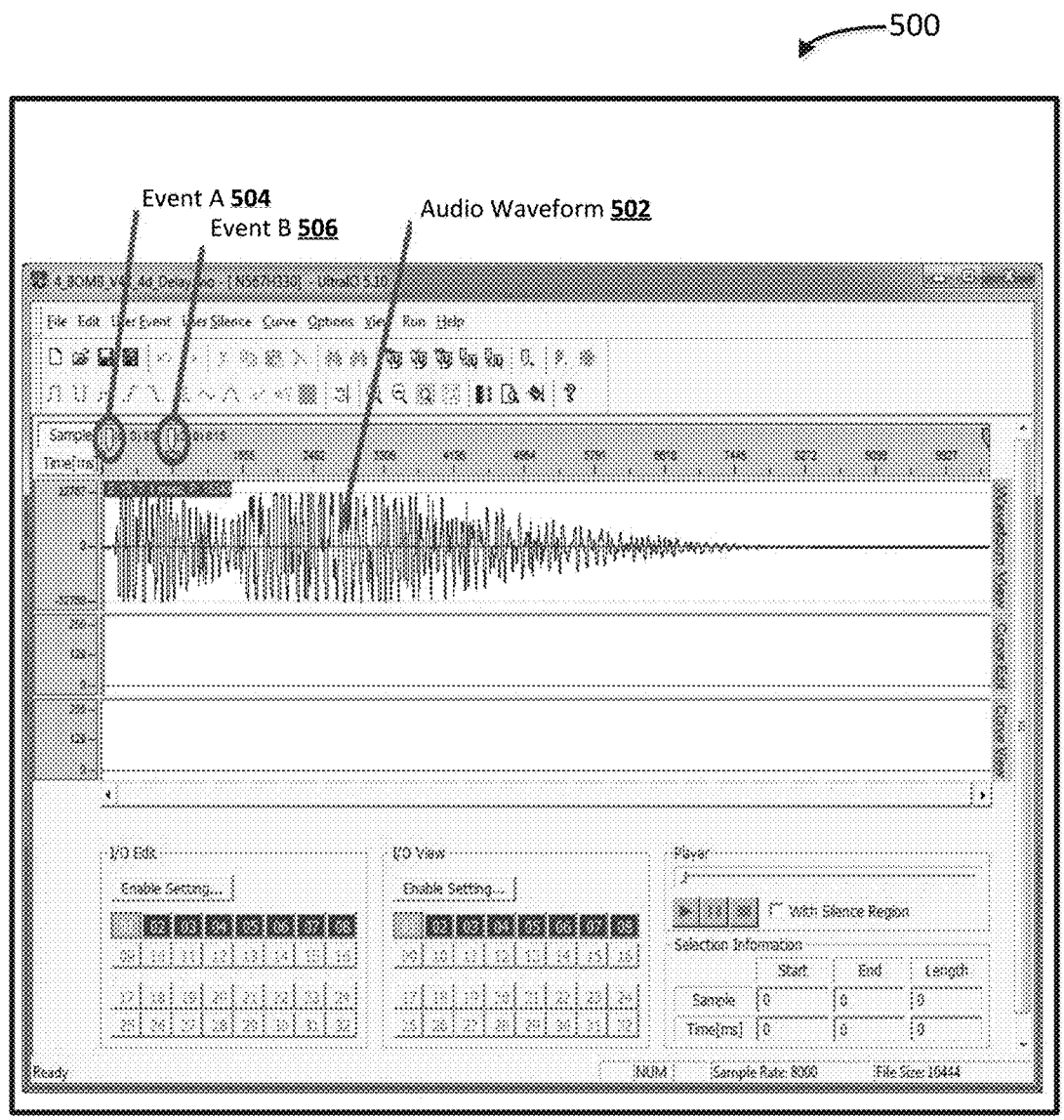
FIGS. 5-8 illustrate various options and techniques for synchronizing sound and non-sound output at the baby swing or other children's product according to certain example embodiments of the disclosure.

FIG. 5 depicts an illustration of a media file 500 that may be loaded into sound and vibration pattern storage medium 404. In one example embodiment, a user interface may be used to create, edit, customize, or configure media files for operation with the children's soothing device. The media file 500 is of an example heartbeat audio waveform 502 along with embedded codes or non-sound events (504, 506) to turn on/off the vibration motor and/or lights on the children's soothing device in sync with the playing of the heartbeat audio waveform 502. While the example embodiment of FIG. 5 presents an audio waveform of a heartbeat or simulated heartbeat, in other example embodiments, the audio waveform could be that of music, nature sounds, white noise, a car ride, a stroller ride (e.g., sound of the stroller wheels along the ground with or without nature sounds), rain, wind, waves or other ocean or beach-related sounds, playful sounds, bells, and/or the like.

In certain example embodiments, the example audio waveform 502 or any other desired media file of an audio waveform may contain one or more non-sound event markers inserted into the media file 500. Each non-sound event marker can be associated with a specific action (e.g., turn on the vibration motors, turn off the vibration motors, turn on the lights, turn off the lights, turn on a particular one or more of multiple vibration motors, turn off a particular one or more of multiple vibration motors, turn on a particular one or more of multiple lights, turn off a particular one or more of multiple lights) to occur at a specific time relative to the playing of the media file. For example, the media file may include non-sound event makers for non-sound event A 504 and non-sound event B 506. In one example, non-sound event A 504 may be a non-sound event that includes instructions to activate a vibrate function (e.g., turning on one or more vibration motors) on the children's soothing device. Similarly, non-sound event B 506 may include instructions to deactivate a vibrate function (e.g., turning off one or more vibration motors) on the children's soothing device. In one example embodiment, one or more of the non-sound events may be synchronized to one or more downbeats. Similarly, one or more non-sound events may be synchronized to one or more upbeats. In one certain example embodiments, the non-sound events may be input, placed within, or otherwise associated with the media file 500 by a user of the children's soothing device or by a manufacturer of the children's soothing device. For example, a manufacturer may provide one or more media files, each with associated non-sound events already inputted therein and stored in the sound and vibration pattern storage 404 of the children's soothing device to ensure synchronization of music, lights, and vibration. In another example embodiment, the non-sound event identification and placement of an associated non-sound event marker into a sound or media file may be performed manually or automatically by a user of the children's soothing device through the use of the user computing device 110 and then loaded onto the sound and vibration pattern storage 404 of the children's soothing device.

In some implementations, the media file may be loaded onto the sound and vibration pattern storage 404 wirelessly or through the use of one or more cables. For example, media files, like media file 500, may be loaded onto the sound and vibration pattern storage 404 via an HDMI cable, a USB cable, and/or the like. In other example embodiments, the media files may be transferred from the user computing device 110 to the children's soothing device for storage onto sound and vibration pattern storage 404 using a Bluetooth connection, a Wi-Fi connection, and/or the like. In another example, the media files may be stored in an external storage device and streamed to the children's soothing device from the user computing device 110.

Once the media files are stored in the sound and vibration pattern storage 404 of the children's soothing device or otherwise transmitted to the children's soothing device, a microprocessor 402 may be used to access one of the media files and generate music and/or sounds. For example, microprocessor 402 may initiate playback of one of the multiple media files stored in the sound and vibration pattern storage 404. The data for the audio portion of the media file can be delivered to a speaker 412 communicably coupled to the microprocessor 402.

The pattern for turning on and off the vibration motor 414, the lights 416, or both can be programmed to synchronize with the music and/or other sound (e.g., heartbeat, nature sounds, white noise, a car ride, a stroller ride (e.g., sound of the stroller wheels along the ground with or without nature sounds), rain, wind, waves or other ocean or beach-related sounds, playful sounds (e.g., playful songs), bells etc.) produced by the children's soothing device, such as via the media files 500. As described above, the patterns determining when a vibration motor 414 may be turned on or off and/or when lights 416 may be turned on or off may be defined based on markers stored in association with the media files in, for example the sound and vibration pattern storage 404 (e.g., RAM 406 and/or ROM 408), and/or the memory of the user computing device 110. In certain example embodiments, the microprocessor 402 can determine a time associated with each stored marker. In turn, when, for example, playback of the media file 500 reaches a first non-sound event marker (e.g., non-sound event A 504), the microprocessor 402 may transmit a signal to activate the vibration motor 414, a particular motion 432 of the children's soothing device (e.g., swinging motion, rocking motion, circular motion, another patterned or random motion, vibration (high vibration, low vibration, etc.)), one or more of the lights 416 provided at the children's soothing device and/or the like. Similarly, when the playback of the media file reaches a second non-sound event marker (e.g., non-sound event B 506), microprocessor 402 may transmit a signal to turn on another one or more of the vibration motors 414, motions 432, and/or lights 416 or may alternatively transmit a signal to turn off one or more of the vibration motors 414, motions 432, lights 416, or the like. For example, the microprocessor 402 may transmit a signal to activate a particular motion 432 of the children's soothing device in response to media playback reaching the first marker and transmit a signal turning on one or more of the lights 416 in response to media playback reaching the second marker.

The user interface of FIG. 5 may be a graphical user interface (GUI) for a computer program executed on user computing entities 110 and/or management computing entity 102. The computer program may, for example, allow for creating, editing, customizing, and/or configuring media files for operation with the children's soothing device. In certain example embodiments, the media files may be sound files, such as ambient noise sounds, heartbeat sounds, nature sounds, music, voice recordings, a car ride, a stroller ride (e.g., sound of the stroller wheels along the ground with or without nature sounds), rain, wind, waves or other ocean or beach-related sounds, playful sounds (e.g., a playful song), bells, and/or the like. The program may allow the users to manipulate and perform various operations on different media files. For example, the GUI of the program may be used to place one or more non-sound event markers at particular portions or times associated with playback of the media file. For example, a user may place markers defining non-sound event A 504 and non-sound event B 506 at times associated with particular points of the audio waveform 502. For example, as described above, the user may choose to place a marker at a downbeat of a song. Alternatively, the user may choose to place a marker at custom user-defined location (e.g., beginning of the song, 13 seconds into the song, one minute into the song, etc.). In some implementations, the GUI may also allow users to edit the audio waveform 502 by removing, combining, or overlapping all or portions of audio waveforms. In certain example embodiments, the GUI may be accessible directly or indirectly from a user computing device 110 (e.g., in communication with the management computing entity 102 via the network 105). In other examples, the GUI may be associated with a program installed and executed on user computing device 110 or installed and executed on a remote server in communication with user computing device 110.

In other example embodiments, the microprocessor 402 may perform one or more sound processing operations to automatically determine placement of non-sound event markers into a media file. For example, the microprocessor 402 may automatically place non-sound event markers at each downbeat in an audio waveform, at each other downbeat, at each node, at each upbeat, and/or at each time a particular instrument makes a specific sound. The example microprocessor 402 may be configured to identify particular patterns (positive peaks, negative peaks, pitch change, gain/db rise, gain/db fall and/or the like) in audio waveforms for placement of the markers. For example, non-sound event markers may be placed at each time a musical instrument sound is played (e.g., guitar, drums, violins, pianos, flutes, etc.). Similarly, non-sound event markers may, for example, be placed at each time a specific piano key is played. In another example, non-sound event markers may be placed at or based on particular vocals. For example, non-sound event markers may be placed by the microprocessor 402 at each time a pitch change or a gain change occurs. In certain example embodiments, the automatic placement of markers by the microprocessor 402 is based on a set of preloaded rules from the manufacturer. The automatic non-sound event marker placement rules may be defined and/or modified/customized by the user via user computing device 110 or management computing entity 102 in other example embodiments.

As discussed with reference to the examples above, synchronization of sound and non-sound events on the children's soothing device can be provided by cues added to the software or readable by the microprocessor 402. One or more stored patterns can be saved and stored in the sound and vibration pattern storage 404 or other memory of the children's soothing device. The children's soothing device can also be configured to deliver music and/or sounds from a separate device with stored music and/or sounds that may be connectable (wired or wirelessly) to the children's soothing device and controllable by the microprocessor 402 so that a user can select and play or deliver specific desired sounds and/or music. The children's soothing device can have one or more speakers 412 communicably coupled to the microprocessor 402 that receive the sound and/or music data for playback (e.g., from the sound and vibration pattern storage 404 via the microprocessor 402) at the children's soothing device. The children's soothing device can be arranged so that the music and/or sounds can be selected and controlled entirely on the children's soothing device, entirely on a housing coupled to the children's soothing device, on a separate (e.g., add-on) device coupled to the children's soothing device, or some combination thereof.

When the microprocessor 402 is operated to play a stored media file that includes sound or music, such as from the sound and vibration pattern storage 404, the microprocessor 402 reads the audio waveform 502 data from memory and uses it to directly or indirectly drive the speaker 412. When the microprocessor 402 encounters one of the non-sound event markers or embedded codes in the waveform data, it will immediately act on the non-sound event and, for example, signal the lights 416 or vibration motor 414, to turn on or off based on the code or marker. The embedded codes or non-sound events can be frequent, infrequent, simple, or complex. In one example, the microprocessor can read non-sound events or codes according to the following table:

TABLE A

| Operation # | Action |
| --- | --- |
| 1 | Turn on vibration - high |
| 2 | Turn on vibration - low |
| 3 | Turn off vibration |
| 4 | Turn on Red LED |
| 5 | Turn on Green LED |
| 6 | Turn on Blue LED |
| 7 | Turn off all LEDs |

The above table depicts some exemplary mapping to non-sound events. Many other examples are certainly possible within the scope of the present disclosure. In certain example embodiments, the users may be able to define or change the mapping using the user computing devices 110 and/or management computing entity 102. The non-sound events or embedded codes can be time-positioned within the audio or sound waveform data in order to synchronize the non-sound output with the sound output. For example, codes can be embedded that are read by the microprocessor 402 to indicate when a non-sound output such as a vibration and/or lighting event should be activated or deactivated. This method or technique effectively synchronizes the sound and non-sound outputs.

Figure 6:

FIG. 6 depicts a music sheet or music notation 600 of the song "Ah, vous dirai je, Maman." As shown, the song contains a non-sound event marker for non-sound event C 602 and non-sound event D 604. In this example, the non-sound event markers are placed at the first beat of each measure. In one example, the microprocessor 402 may turn on the vibration motor 414 at low speed during the first beat of each measure. In this example, non-sound event C 602 begins with note C3 and stops at note C4 (the first two notes in the bass clef). During that period, the vibration motor 414 may be, for example, turned on. Non-sound event D 604 begins with note E4 and stops at note C4 (the next two notes in measure 3). Similarly, during that period, the vibration motor 414 may be also turned on. The microprocessor 402 may be configured to perform any of the operations of table A in response to playback of the song reaching the non-sound event C 602 and/or non-sound event D 604 for a specific duration.

The sound data or waveform files can be modified to include Musical Instrument Digital Interface (MIDI) data files as embedded non-sound events in the waveform. For example, the non-sound events can specify for the microprocessor 402 which device (e.g., one or more of the vibration motors 414 or one or more of the lights 416) to activate or deactivate, at what intensity/color and the time and duration of activating the vibration motor 414 or lights 416. For example, the non-sound event can specify that a red light 416 is to be turned on for 10 seconds at the first downbeat of a song. Similarly, the non-sound event may specify that vibration motor 414 is activated at 1 minute after the beginning of the song and that the vibration motor 414 is turned off after 20 seconds from the activation. Similarly, the waveform files may also include WAVE files as embedded code to perform the same functions.

Figure 7A:
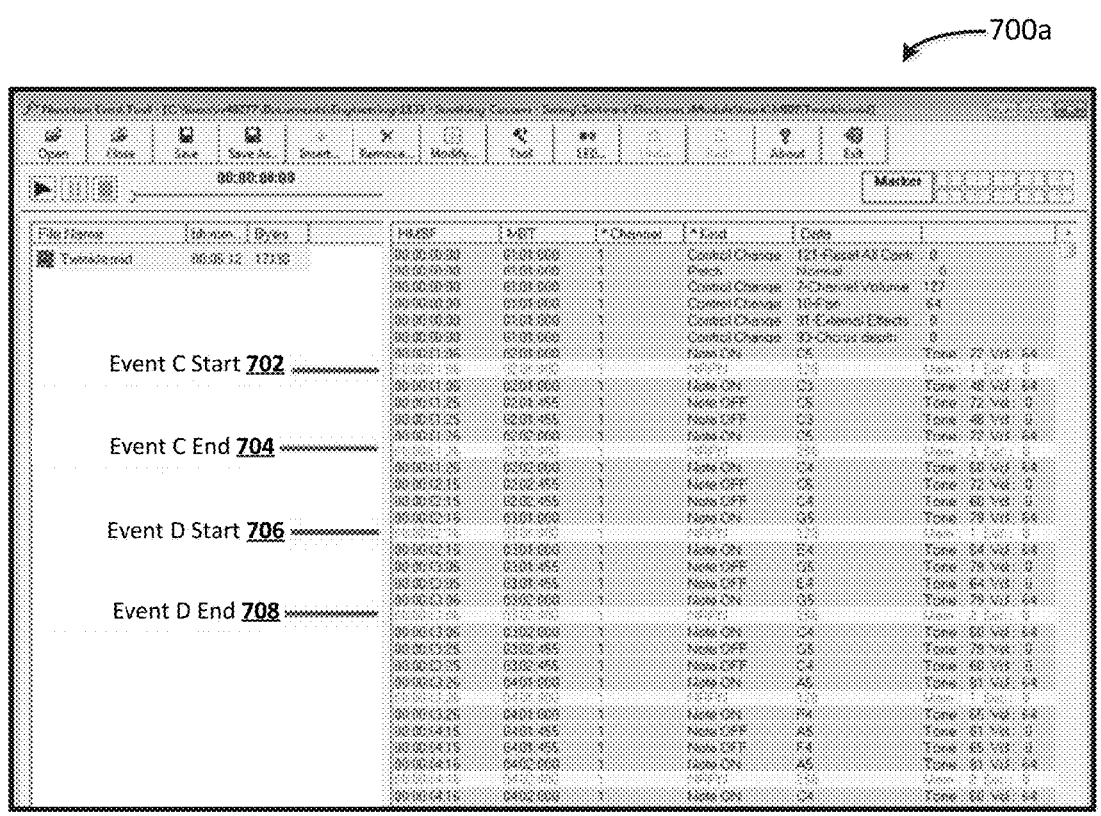
Figure 7B:

FIGS. 7A and 7B depict a GUI for viewing and editing a MIDI sequence 700A and 700B to include non-sound events for the children's soothing device according to one example embodiment of the disclosure. For example purposes only, the shown sequences are associated with the song of FIG. 6, however any other song can be similarly edited to include non-sound event instructions. As shown in the MIDI sequence 700A of FIG. 7A, non-sound event C start 702 and non-sound event C end 704 are identified. In one example, the non-sound event C start 702 is associated with the turning a non-sound device (e.g., one or more vibration motors and/or one or more lights 416) on and non-sound event C end 704 is associated with turning the non-sound device off. For example, non-sound event C start 702 can denote turning on vibration motor 414 at high intensity and non-sound event C end 704 denotes turning off the vibration motor 414. Similarly, non-sound event D start 706 and non-sound event D end 708 may denote a period where the vibration motor 414 is turned on. In one example, the motion and/or vibration motor 414 may be turned on between non-sound event C start 702 and non-sound event C end 704 at a low intensity and turned on between event D start 706 and event D end 708 at a high intensity. Attentively or simultaneously, instructions may be provided by the non-sound events in the files such that one or more of the lights 416 may be colored red between non-sound event C start 702 and non-sound event C end 704 and green between non-sound event D start 706 and non-sound event D end 708. Alternatively, instead of the lights 416 changing color, red lights 416 may be activated between non-sound event C start 702 and non-sound event C end 704 and green lights 416 may be activated between non-sound event D start 706 and non-sound event D end 708.

In certain example embodiments, multiple non-sound devices at the children's soothing device may be turned on in response to reaching a non-sound event during playback of a sound file. For example, responsive to reaching non-sound event C start 702, the microprocessor 402 may turn on both the vibration motor 414 and one or more of the lights 416. Similarly, responsive to reaching non-sound event C end 704 the microprocessor 402 may turn off both the vibration motor 414 and lights 416. Various combinations of actions that are triggered by each non-sound event marker may be customized by the manufacturer or the users. In one example, a user computing device 110 may access a GUI such as 700A and/or 700B to edit or create a MIDI sequence with non-sound event markers. The sequence then may be loaded onto the children's soothing device, such as at the sound and vibration pattern storage 404, along with the associated media files.

Figure 8:
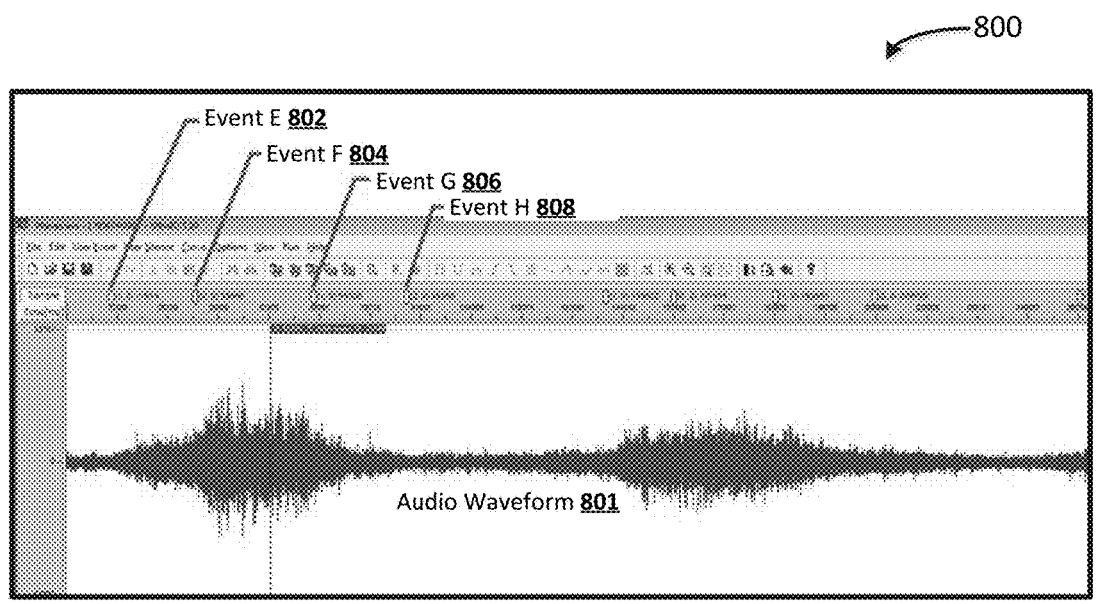
Figure 9A:
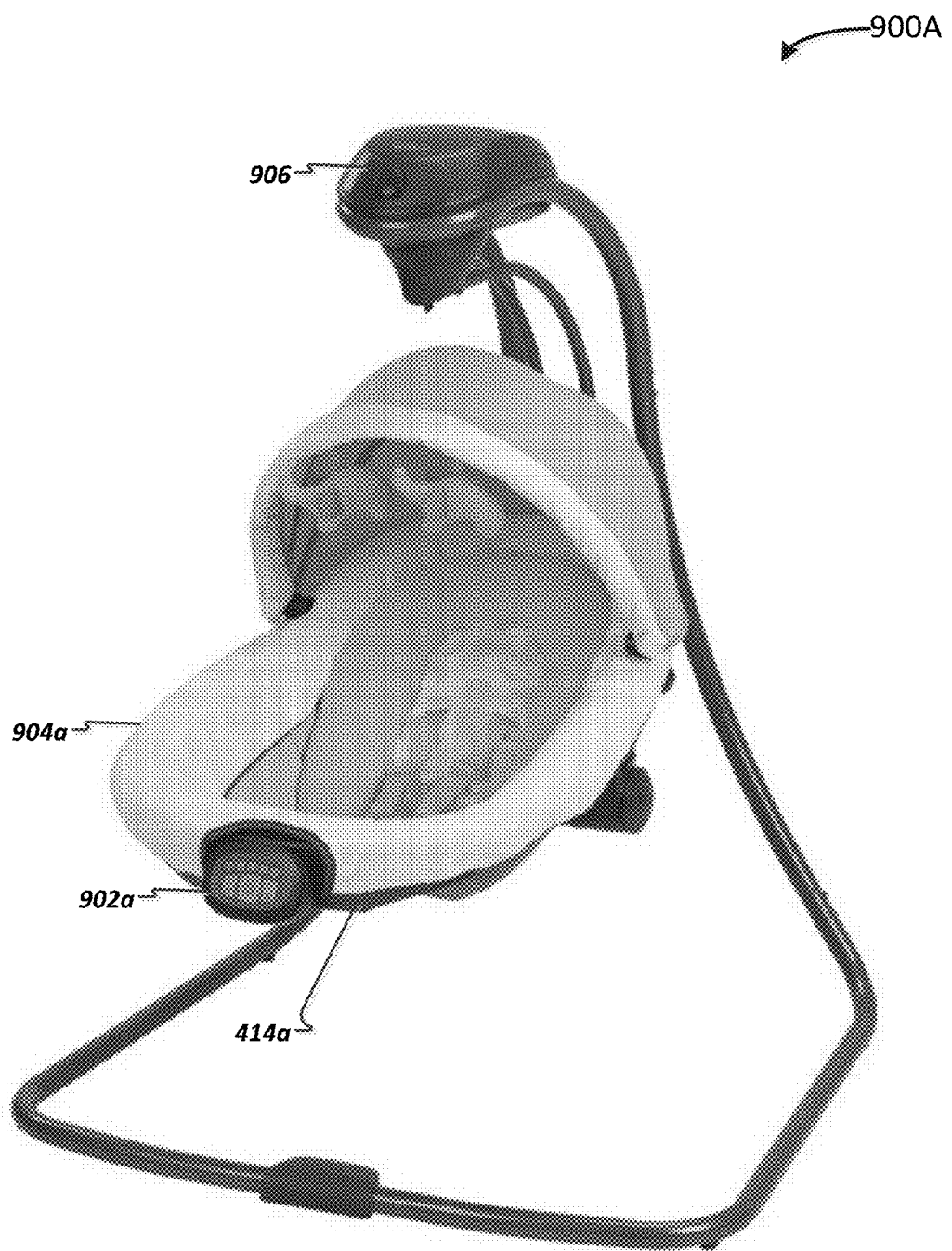
FIGS. 9A-H depict exemplary children's soothing devices in accordance with example embodiments of the disclosure.
Figure 9B:
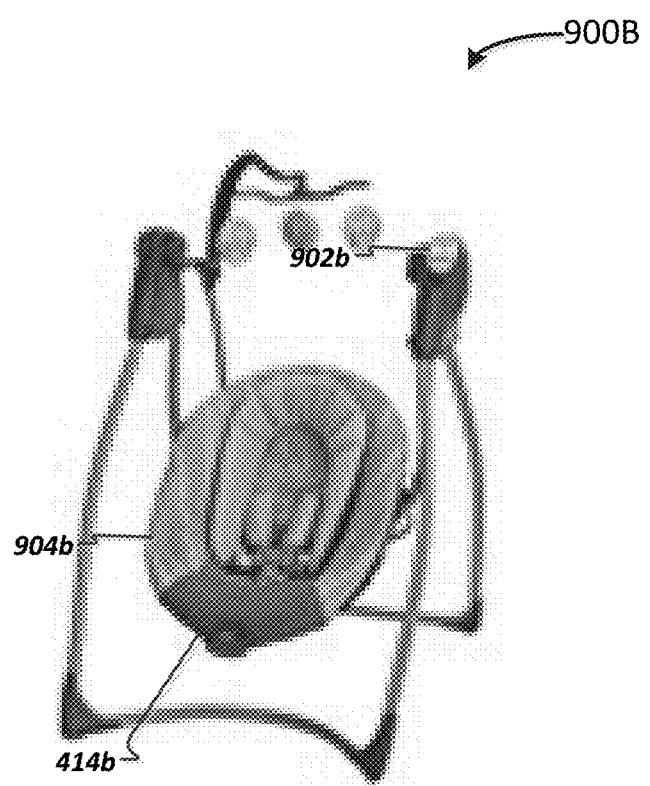
Figure 9C:
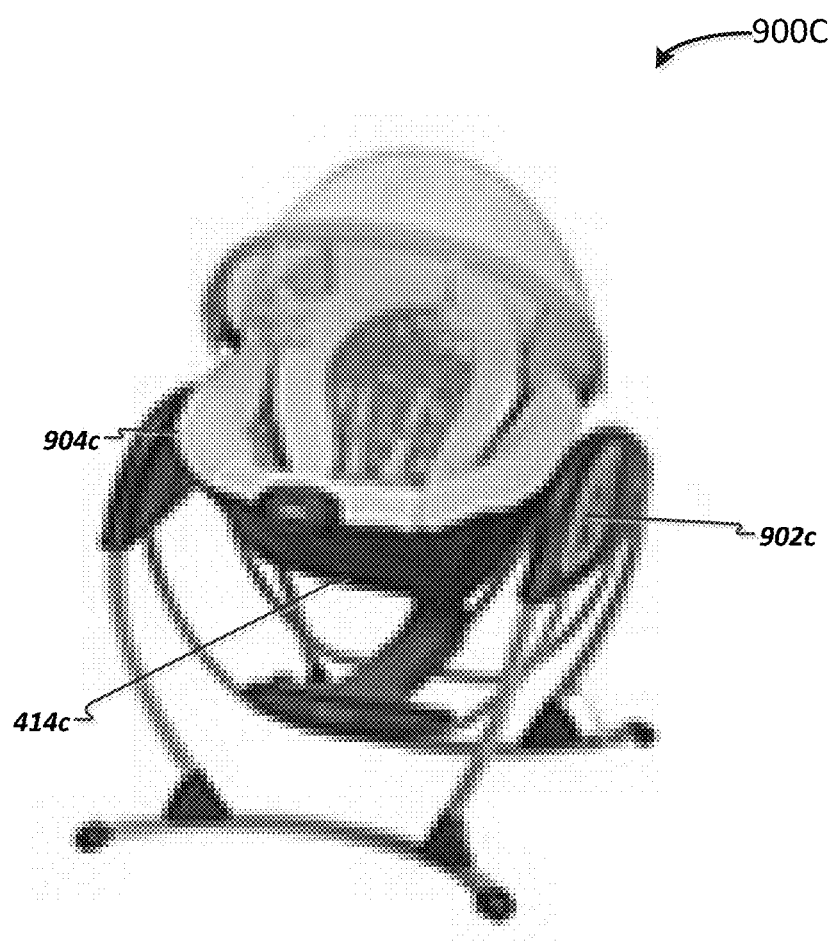
Figure 9D:
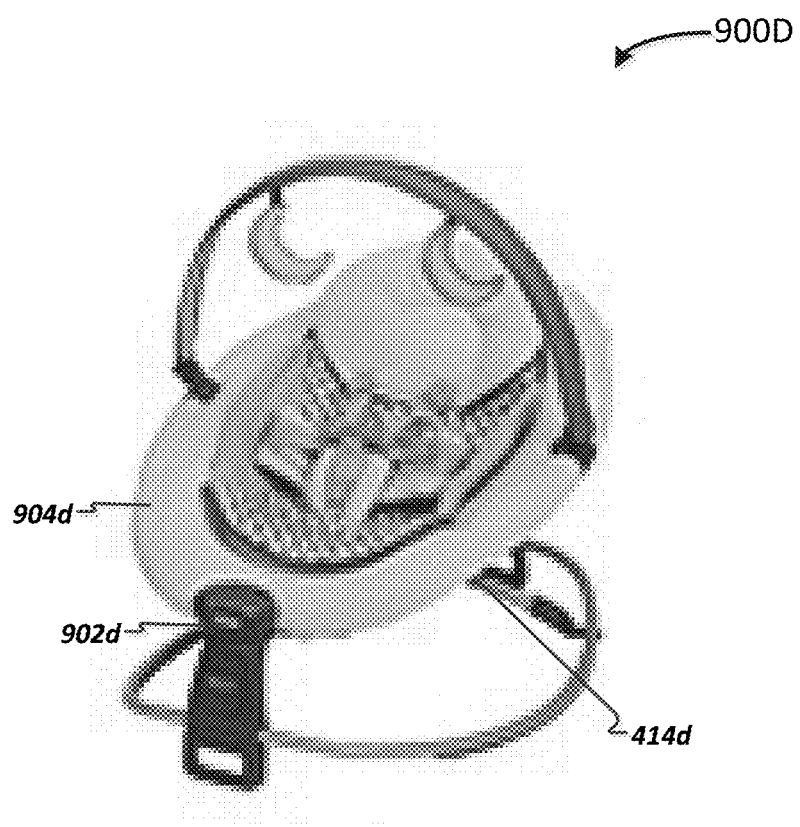
Figure 9E:
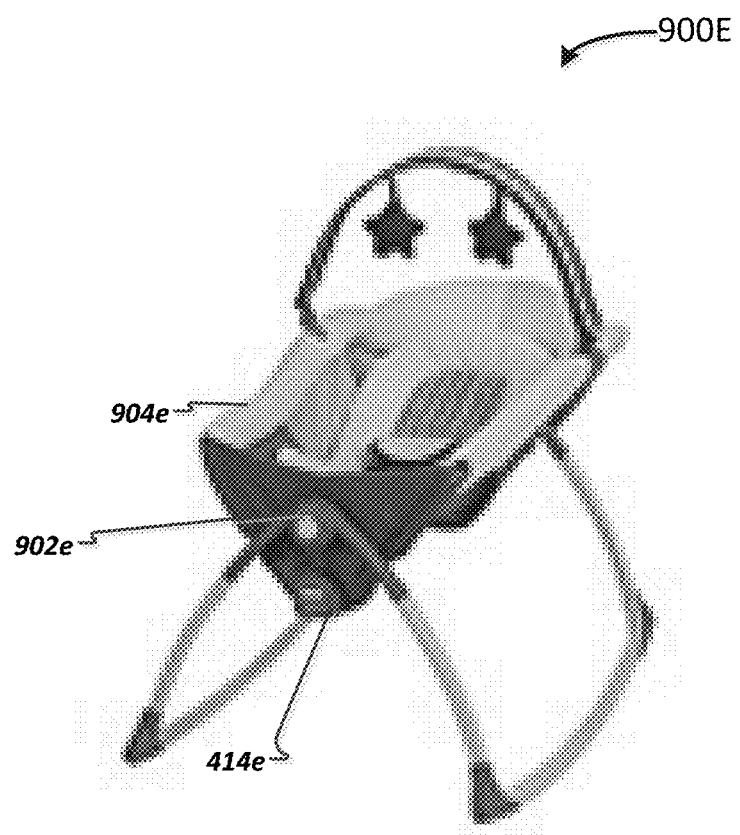
Figure 9F:
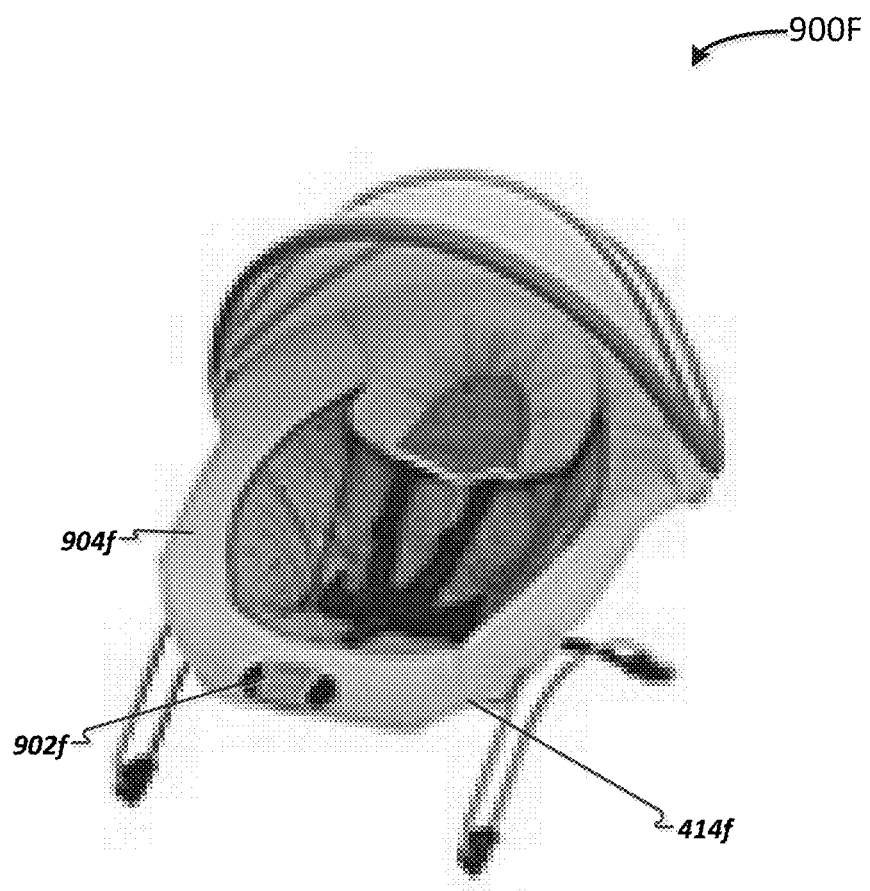
Figure 9G:
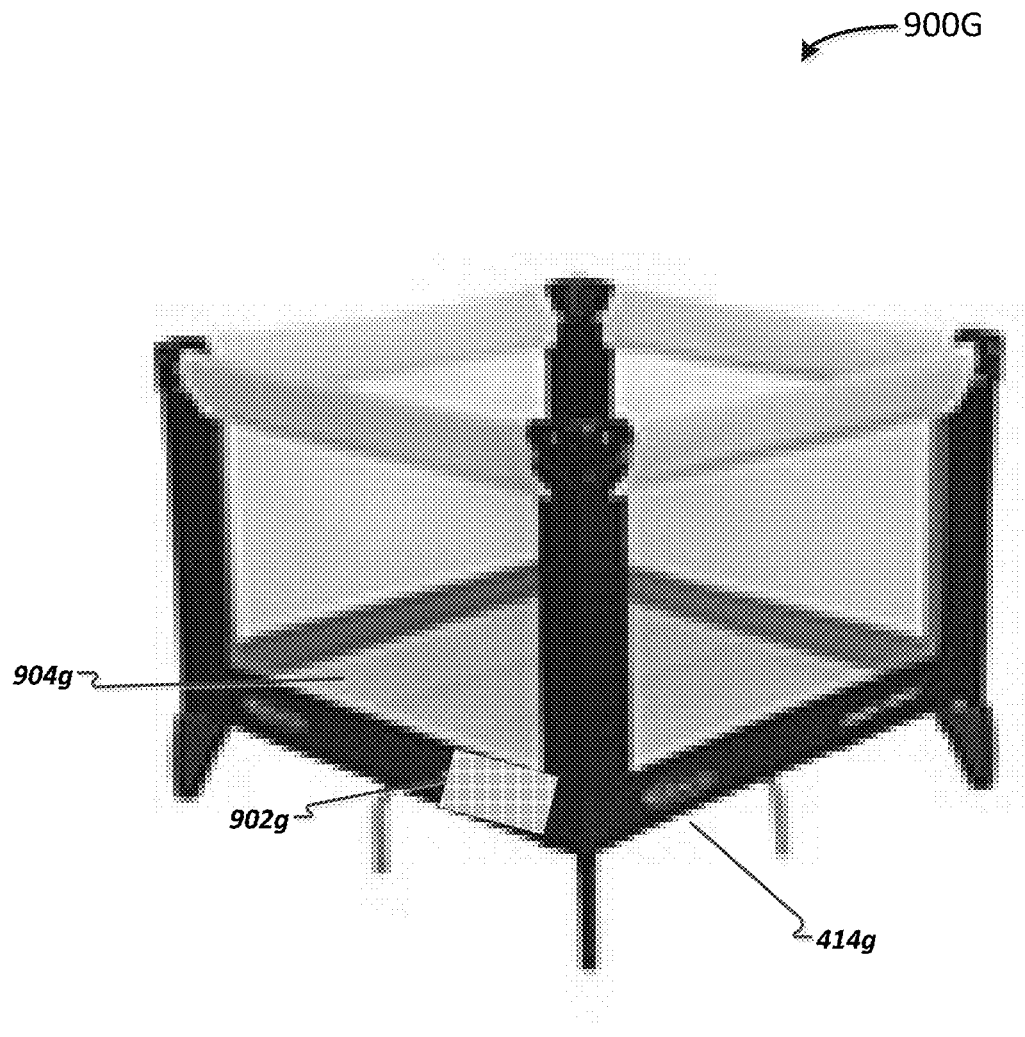
Figure 9H:
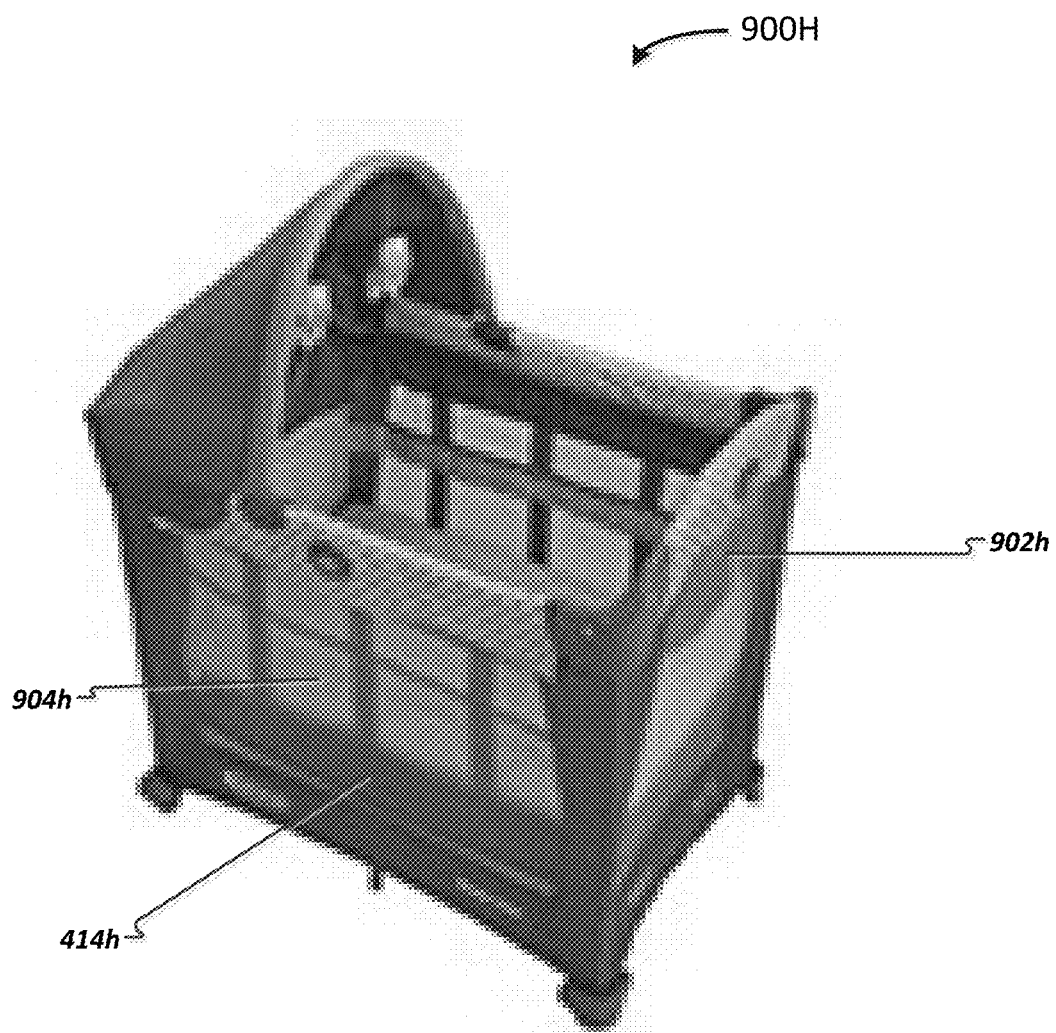

FIG. 8 depicts an illustration of a media file with non-sound event markers that may be loaded into sound and vibration pattern storage 404 according to one example embodiment of the disclosure. Referring to FIG. 8, in one example, a user interface 800 may be used to create, edit, customize, or configure media files to include, remove, move, or modify non-sound event markers within the media files for operation with the children's soothing device. The illustrated media file of FIG. 8 is an example ocean waves audio waveform 801 along with embedded codes or non-sound event markers (802, 804, 806, 808) to turn on/off the vibration motor 414 and/or the lights 416 at predetermined times within the audio waveform 801 such that they are in synch with the sounds of the ocean waves.

The audio waveform 801 may contain one or more non-sound event markers, each being associated with a specific time relative to playback of the audio waveform 801. For example, the media file may include non-sound event markers for non-sound event E 802, non-sound event F 804, non-sound event G 806, and non-sound event H 808. In one example, non-sound event E 802 may be a non-sound event that includes instructions to the microprocessor 402 to turn on the vibration motor 414 on the children's soothing device at low intensity level (when multiple intensity levels are available). Similarly, non-sound event F 804 may include instructions for the microprocessor 402 to turn on the vibration motor 414 on the children's soothing device at a high intensity level (when multiple intensity levels are available). In one example, non-sound event E 802 may be a non-sound event that includes instructions for the microprocessor 402 to turn on the vibration motor 414 on the children's soothing device at low intensity again. Similarly, non-sound event F 804 may include instructions for the microprocessor 402 to turn on the vibration motor 414 on the children's soothing device at a high intensity. In one example, non-sound event G 806 may be a non-sound event that includes instructions for the microprocessor 402 to turn on the vibration motor 414 on the children's soothing device at low intensity again. Finally, non-sound event H 808 may include instructions for the microprocessor 402 to turn off the vibration motor 414 on the children's soothing device.

FIGS. 9A-H depict exemplary children's soothing devices 900A-H (e.g., a motorized swing (900A-B, motorized glider 900C, motorized rocker 900E, motorized bouncer 900D and 900F, playard or crib 900G, or bassinet 900H) in accordance with example embodiments of the disclosure. Each children's soothing device 900A-H may include a control panel 902a-h for manually controlling various aspects of the children's soothing device 900A-H (e.g., volume, light intensity, light colors, sound playback (with or without non-event sound synchronization). In certain example embodiments, the control panel 902a-h may be disposed on an outer surface of a housing that encloses at least a portion of the electrical components of the system 400 discussed in FIG. 4 above. Each children's soothing device 900A-H may also include a child contacting surface 904a-h, such as a cradle, seat, or bedding surface for placement of a child or an infant within the children's soothing device 900A-H. Each of the children's soothing devices 900A-H may also include one or more vibration motors 414a-h. In one example embodiment, the vibration motor may be separate from the housing for the control panel 902a-h and in close proximity and or contact with the child contacting surface 904a-h. Alternatively, the one or more vibration motors 414a-h may be disposed on the frame of the device 900A-H or within the housing for the control panel 902a-h. Each of the children's soothing devices 900A-H may also include one or more lights 416 (not shown) either coupled to, disposed along, or removably coupled to any portion of the outer surface of the respective children's soothing device 900A-H.

Figure 10:
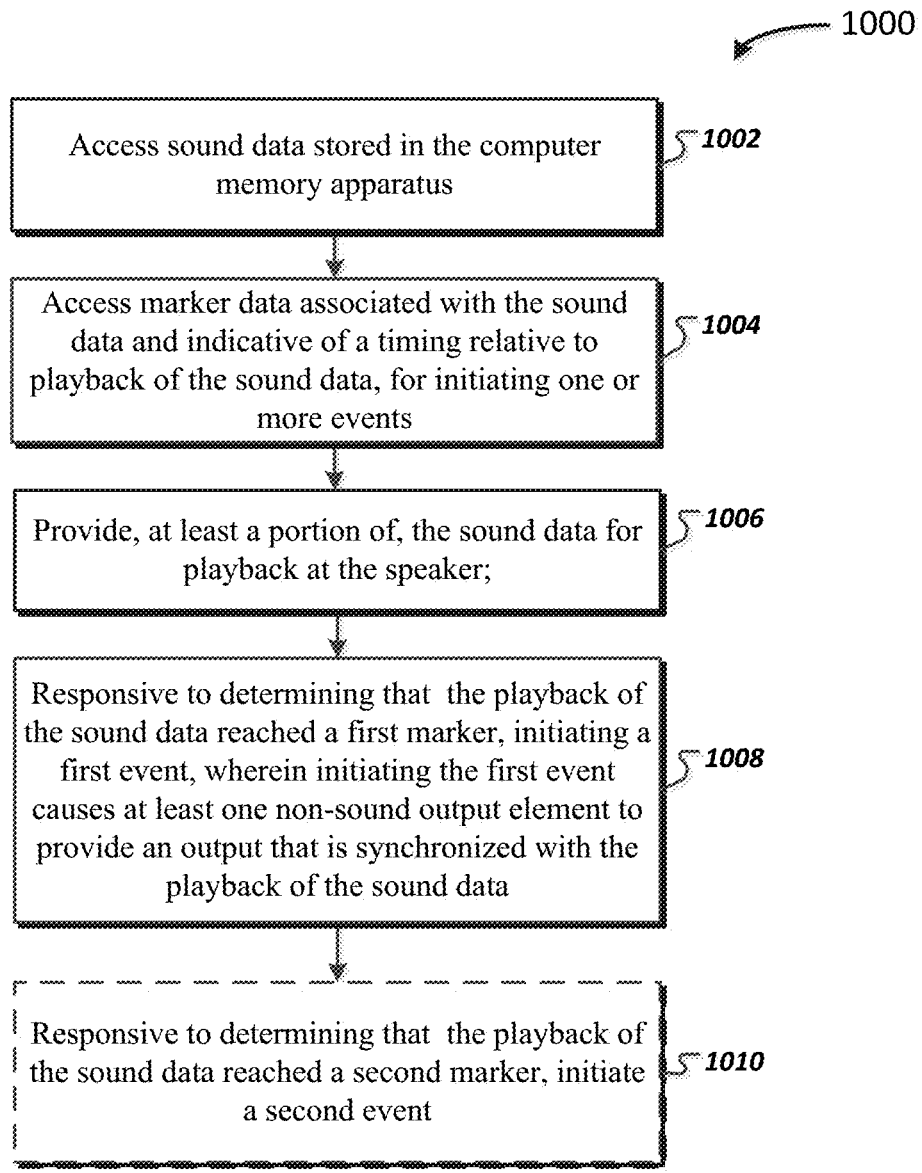
FIG. 10 is a flowchart illustrating a method for synchronizing sound and non-sound output on a baby swing or other children's product according to one example embodiment of the disclosure.

FIG. 10 is a flowchart of process 1000 for synchronizing sound and non-sound output at a children's soothing device in accordance with one example embodiment of the disclosure. Referring now to FIGS. 1-4, 8, and 10, the example process 1000 begins at 1002 by accessing sound data stored in the computer memory apparatus. For example, the microprocessor 402 may access sound data stored in the sound vibration pattern data storage 404, RAM 406 and/or program ROM 408. The process can proceed to 1004 where non-sound event marker data associated with the sound data and indicative of a timing relative to playback of the sound data is accessed in order to initiate one or more non-sound events. For example, the microprocessor 402 may access non-sound event marker data stored in sound and vibration pattern data storage 404, RAM 406 and/or program ROM 408. The data may specify a time associated with each non-sound event marker identified from the non-sound event marker data (802, 804, 806, 808).

At 1006, at least a portion of the sound data can be provided for playback at the speaker. For example, the microprocessor 402 may provide instructions or data configured to cause speaker 412 to playback at least a portion of a song or sounds associated with the sound data. Responsive to determining that the playback of the sound data reached a first marker, a first non-sound event can be initiated, wherein initiating the first non-sound event causes at least one non-sound output element (e.g., one or more vibration motors 414 or one or more lights 416) to provide an output that is synchronized with the playback of the sound data at 1008. For example, the microprocessor 402 may synchronize playback of the sound with activation of lights 416 and/or vibration motors 414 within the children's soothing device, as described above. For example, responsive to reaching the first non-sound event marker during playback of the sound data, the microprocessor 402 may turn on the vibration motor 414 and/or one or more of the lights 416.

In certain example embodiments, the process may continue with optional step 1010 where a second non-sound event is initiated in response to determining that the playback of the sound data reached a second non-sound event marker. For example, responsive to reaching the second non-sound event marker during playback of the sound data, the microprocessor 402 may initiate one or more of the vibration motors 414 at a higher or lower intensity, turn off the vibration motors 414, activate/deactivate the lights 416, alter colors of the lights 416 and/or the like. The process may continue to process additional non-sound event markers in a manner similar to the above until the end of the sound file is reached.

Because of nature of soothing systems, it is often desirable to manufacture such systems at a low cost to meet consumers' demands. Lower costing vibration motors, solenoids, and DC motors in general are associated with lower performance metrics. For example, such motors and solenoids are associated with high delays and slow response times. The children's soothing device may factor in such delays when activating the vibration motors 414. For example, the signal from the microprocessor 402 instructing the vibration motor 414 to move the child contacting surface 904*a-h* may be sent prior to reaching the marker. For example, if a vibration motor 414 is associated with a three-second delay, the signal may be provided by the microprocessor 402 three seconds early (three seconds prior to the playback reaching the marker) to ensure that the movement and sound are synchronized. Accordingly, highly accurate synchronization may be achieved with low-end and low-cost components.

Although example embodiments of the disclosure have been described, one of ordinary skill in the art will recognize that numerous other modifications and alternative embodiments are within the scope of the disclosure. Furthermore, while various example implementations and architectures have been described in accordance with example embodiments of the disclosure, one of ordinary skill in the art will appreciate that numerous other modifications to the example implementations and architectures described herein are also within the scope of this disclosure.

Furthermore, the exemplary embodiments disclosed above have been discussed with reference to certain specific sound files and sound file storage standards. The use of specific sound files and sound file storage standards above and in the claims is not intended to be limiting. Other types of sound files and sound file storage standards are within the scope of this disclosure and the claims.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block diagrams and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method for synchronizing sound and non-sound output at a child soothing device comprising:
    providing the child soothing device comprising:
        a frame;
        a child contacting surface operably coupled to the frame;
        a speaker; and
        a vibration device operable to vibrate the child contacting surface;
        a controller operably coupled to the child soothing device and comprising a memory and a processor;
    accessing, by the processor, a sound data file stored in the memory;
    accessing, by the processor, a non-sound event marker data in the memory for initiating one or more non-sound events;
    generating, by the processor, a sound output at the speaker based on the sound data file;
    identifying, by the processor and based at least on an evaluation of the sound data file, a first non-sound event marker in the sound data file; and
    activating, by the processor and based on the first non-sound event marker in the sound data file, the vibration device.

2. The method of claim 1, wherein activating the vibration device further comprises, activating the vibration device at one of a plurality of vibration levels based at least on the first non-sound event marker.

3. The method of claim 1, wherein the child soothing device further comprises at least one light source, and wherein an activation state of at least one of the at least one light source is changed by the processor based at least on the first non-sound event marker.

4. The method of claim 3, wherein the activation state of the at least one light source comprises one or more of turning each of the at least one light source on, turning each of the at least one light source off, turning a portion of the at least one light source on, turning a portion of the at least one light source off, dimming at least a portion of the at least one light source, and changing a color emitted by a portion of the at least one light source.

5. The method of claim 1, wherein the vibration device comprises a vibration motor.

6. The method of claim 1, further comprising:
    identifying, by the processor and based at least on an evaluation of the sound data file, a second non-sound event marker in the sound data file after the first non-sound event marker;
    initiating, by the processor, a second non-sound event at the child soothing device based on the second non-sound event marker.

7. The method of claim 6, wherein initiating the second non-sound event comprises deactivating the vibration device.

8. The method of claim 6, wherein initiating the second non-sound event comprises reducing an intensity level of the vibration device.

9. The method of claim 6, wherein initiating the second non-sound event comprises increasing an intensity level of the vibration device.

10. The method of claim 6, wherein the child soothing device further comprises at least one light source and wherein initiating the second non-sound event comprises activating the at least one light source.

11. The method of claim 6, wherein the child soothing device further comprises at least one light source and wherein initiating the second non-sound event comprises changing a state of the at least one light source.

12. The method of claim 1, wherein the child soothing device is one of a motorized swing, a motorized glider, a motorized rocker, a motorized bouncer, a playard, a crib, a car seat, a stroller, an infant carrier, or a bassinet.

13. The method of claim 1, wherein the child soothing device is a motorized swing comprising a seat, and wherein the child contacting surface is defined by the seat.

14. The method of claim 1, wherein the sound data file comprises data for playback of one of a heartbeat or a simulated heartbeat.

15. The method of claim 1, wherein the sound data file comprises data for playback of a song.

16. The method of claim 1, wherein the sound data file comprises data for playback of one or more of: a heartbeat, a simulated heartbeat, a song, a white noise, a car ride, a stroller ride, a rain sound, a wind sound, a waves sound, a playful sound, and at least one bell sound.

17. A system comprising:
    a child soothing device comprising:
        a speaker; and
        a vibration motor operable to vibrate at least a portion of the child soothing device;
    at least one memory operable to store computer-executable instructions; and
    at least one processor configured to access the at least one memory and execute the computer-executable instructions to:
        access a sound data file stored in the memory, wherein the sound data file comprises a plurality of non-sound event markers;
        generate a sound output at the speaker based on sound data in the sound data file;

identify, based at least on an evaluation of the sound data file, a first non-sound event marker in the sound data file; and activate, by the processor and based on the first non-sound event marker, the vibration motor.

18. The system of claim 17, further comprising a child contacting surface, wherein the vibration motor is operable to vibrate the child contacting surface.

19. The system of claim 17, wherein the processor is further configured to access the memory and execute the computer-executable instructions to:

identify, based at least on an evaluation of the sound data file, a second non-sound event marker in the sound data file after the first non-sound event marker; and initiate a second non-sound event based on the second non-sound event marker at the child soothing device.

20. The system of claim 17, wherein the child soothing device is one of a motorized swing, a motorized glider, a motorized rocker, a motorized bouncer, a playard, a crib, a car seat, a stroller, an infant carrier, or a bassinet.

* * * * *